United States Patent
Duronio

(10) Patent No.: US 10,179,144 B2
(45) Date of Patent: Jan. 15, 2019

(54) FORMULATIONS AND COMPOSITIONS FOR REJUVENATION OF THE BODY

(71) Applicant: Roger F. Duronio, Bogota, NJ (US)

(72) Inventor: Roger F. Duronio, Bogota, NJ (US)

( * ) Notice: Subject to any disclaimer, the term of this patent is extended or adjusted under 35 U.S.C. 154(b) by 0 days.

(21) Appl. No.: 15/866,605

(22) Filed: Jan. 10, 2018

(65) Prior Publication Data

US 2018/0221397 A1 Aug. 9, 2018

Related U.S. Application Data

(60) Provisional application No. 62/455,776, filed on Feb. 7, 2017.

(51) Int. Cl.
| | |
|---|---|
| *A61K 31/706* | (2006.01) |
| *A61K 31/09* | (2006.01) |
| *A61K 31/138* | (2006.01) |
| *A61K 31/197* | (2006.01) |
| *A61K 31/366* | (2006.01) |
| *A61K 31/4365* | (2006.01) |
| *A61K 31/4439* | (2006.01) |
| *A61K 31/519* | (2006.01) |
| *A61K 31/616* | (2006.01) |
| *A61K 31/714* | (2006.01) |
| *A61K 9/00* | (2006.01) |

(52) U.S. Cl.
CPC .......... *A61K 31/706* (2013.01); *A61K 9/0053* (2013.01); *A61K 31/09* (2013.01); *A61K 31/138* (2013.01); *A61K 31/197* (2013.01); *A61K 31/366* (2013.01); *A61K 31/4365* (2013.01); *A61K 31/4439* (2013.01); *A61K 31/519* (2013.01); *A61K 31/616* (2013.01); *A61K 31/714* (2013.01)

(58) Field of Classification Search
CPC .. A61K 31/706; A61K 31/519; A61K 31/714; A61K 31/197; A61K 31/09; A61K 31/4439; A61K 31/616; A61K 31/366; A61K 31/4365; A61K 31/138; A61K 9/0053

USPC ............................................ 514/43; 435/375
See application file for complete search history.

(56) References Cited

U.S. PATENT DOCUMENTS

| | | |
|---|---|---|
| 8,747,915 B1 | 6/2014 | Giampapa |
| 8,974,839 B2 | 3/2015 | Giampapa |
| 2008/0214492 A1 | 9/2008 | Hendrix |
| 2010/0239552 A1 | 9/2010 | Mayoux et al. |
| 2013/0142769 A1 | 6/2013 | Smith et al. |

FOREIGN PATENT DOCUMENTS

| | | |
|---|---|---|
| WO | 2015140545 | 9/2015 |
| WO | 2016149277 | 9/2016 |

OTHER PUBLICATIONS

Shah RC. U.S. National Library of Medicine. ClinicalTrials.gov. Study NCT00597376 on Date: May 20, 2013 (v6). https://clinicaltrials.gov/ct2/history/NCT00597376?V_6=View#Study (Year: 2013).*
Cerefolin NAC. http://www.empr.com/cerefolin-nac/drug/3420/ (accessed on Apr. 4, 2018) (Year: 2018).*
Poulose et al. Effects of pterostilbene and resveratrol on brain and behavior. Neurochemistry International 89:227-233, 2015. (Year: 2015).*
Weintraub K. The Anti-Aging Pill. MIT Technology Review. Feb. 3, 2015 https://www.technologyreview.com/s/534636/the-anti-aging-pill/ (Year: 2015).*
Basis by Elysium Health. https://www.elysiumhealth.com/supplement-facts (accessed on Apr. 4, 2018) (Year: 2018).*
Goryachkina et al. CYP2D6 is a major determinant of metoprolol disposition and effects in hospitalized Russian patients treated for acute myocardial infarction. Eur J Clin Pharmacol (2008) 64:1163-1173. (Year: 2008).*

* cited by examiner

*Primary Examiner* — Yih-Horng Shiao
(74) *Attorney, Agent, or Firm* — Gearhart Law, LLC

(57) ABSTRACT

The present disclosure describes various formulations and compositions for improving one's vitality and health. The formulations may be particularly useful for treating or alleviating at least erectile dysfunction, increasing muscle mass, and encouraging saliva and tear production. In one example such a composition may include 1-methylfolate, methylcobalamin, n-acetylcysteine, pterostilbene, and nicotinamide riboside.

14 Claims, No Drawings

FORMULATIONS AND COMPOSITIONS FOR REJUVENATION OF THE BODY

CLAIM OF PRIORITY

This application claims priority to U.S. Application 62/455,776 filed on Feb. 7, 2017, the contents of which are herein fully incorporated by reference in its entirety.

FIELD OF THE EMBODIMENTS

The field of the embodiments of the present invention is related to formulations, more specifically, to formulations for rejuvenation of a body including but not limited to dry mouth, dry eyes, erectile dysfunction, anagen-phase body hair, and increased muscle mass.

BACKGROUND OF THE EMBODIMENTS

In humans, aging represents the accumulation of numerous changes to an individual over time. Such changes may encompass physical, psychological, and social changes. For example, reaction time may slow with age and eyesight may begin to falter. Aging is among the greatest known risk factors for most human diseases. Of the roughly 150,000 people who die each day, approximately two thirds die from age-related causes.

The causes of aging are not yet fully understood, however, current theories are assigned to the damage concept, whereby the accumulation of damage (e.g. DNA oxidation) may cause biological systems to fail, or to the programmed aging concept, whereby internal processes (e.g. telomere shortening) may cause aging, or stem cell senescence where the stem cell pool declines in number of active stem cells, and thus daughter cell reproduction, leading to organ failures.

Thus aging may occur as a result of damage which occurs to essential cell components resultant of decrease in levels of key chemical agents or substances involved in cellular regulation and production. Reductions in such key chemical agents are believed to cause damage to the aforementioned DNA in each cell nucleus which thereby reduces the ability of the cell to reproduce itself. This lack of the ability to reproduce may ultimately bring on the aging process. Therefore, the essential problem in aging management is that of maintaining cells such that they will not become damaged or otherwise lose efficiency.

Therefore, it is desirable to have improved compositions that provide nutrients and substances to effectively support optimal cellular functions for the purpose of anti-aging management. The present invention and its embodiments meets and exceeds these objectives.

Review of Related Technology

U.S. Pat. No. 8,747,915 pertains to a dietary supplement composition for oral administration by an individual in the morning, the composition, including (a) a telomere maintenance complex including: Purslane extract (aerial parts); Turmeric rhizome extract (95% curcuminoids); Quercetin dehydrate, Cayenne pepper fruit; Vanadium (as vanadyl sulfate); Fenugreek seed; Astragalus root extract, Omega fatty acid complex including linoleic acid; alpha-linolenic acid; oleic acid borage seed oil gamma-linolenic acid), evening primrose oil fish body oil (eicosapentaenoic acid; docosahexaenoic acid); (b) a calorie restriction mimetics and gene expression complex including Trans-resveratrol (from Polygonum cuspidatum root extract); Pterostilbene Fisetin 50% (Buxus microphlla Sieb (stem and leaf; Alpha lipoic acid, Coenzyme Q-10, Betaine HCl, Sulfur (from methylsulfonylmethane); L-Carnitine tartrate; L-Carnitine HCl, and (c) a free radical scavenger complex, including Green tea leaf extract catechin and polyphenols); Anthocyanins (from bilberry fruit and grape skin extracts).

U.S. Patent Application 2010/0239552 pertains to pharmaceutical combinations comprising an antioxidant agent, an anti-inflammatory agent, and optionally at least one other anti-diabetic agent useful for treating metabolic disorders. This invention also encompasses pharmaceutically acceptable compositions comprising an antioxidant agent, an anti-inflammatory agent, optionally at least one other anti-diabetic agent, and at least one pharmaceutically acceptable carrier. The combinations and compositions of this invention are useful as methods for treating metabolic disorders including diabetes, particularly Type I and Type II diabetes, as well as diseases and disorders associated with diabetes, including but not limited to atherosclerosis, cardiovascular disease, inflammatory disorders, nephropathy, neuropathy, retinopathy, beta.-cell dysfunction, dyslipidemia, LADA, metabolic syndrome, hyperglycemia, insulin resistance, and/or chronic obstructive pulmonary disease in a mammal, particularly a diabetic mammal, and specifically a human patient. This invention is particularly directed to pharmaceutical compositions comprising a lipoic acid, one or more anti-inflammatories selected from the group consisting of diflunisal, diclofenac, dexibuprofen, dexketoprofen, naproxen, and salicylate, and optionally one or more pharmaceutically acceptable carriers. The compositions of this invention are useful as methods for treating metabolic disorders including type II diabetes, insulin resistance, beta-cell dysfunction, and hyperglycemia in a patient, particularly a diabetic patient.

Various compounds are known in the art. However, their makeup and mechanism of action are substantially different from the present disclosure. The other inventions also fail to solve all the problems taught by the present disclosure. At least one embodiment of this invention is presented in the drawings below and will be described in more detail herein.

SUMMARY OF THE EMBODIMENTS

In the human body, tissue-specific or adult stem cells are capable of self-renewal to preserve stem cell pools and differentiation into a variety of effector cells. These defining properties of stem cells are essential for the normal homeostatic maintenance and regenerative repair of tissues throughout the lifetime of an organism. With advancing age, the self-renewal capacity of stem cells invariably declines, eventually leading to the accumulation of unrepaired, damaged tissues in old organisms. The precise mechanism underlying age-dependent decline of stem cell self-renewal is largely unclear, but is fundamentally important to our understanding of aging.

Generally, the present invention and its embodiments provide for compositions and methods relating to rejuvenation of an individual's vitality and general health. Without being bound by any particular theory, it is believed that the present combination of components of the composition are sufficient to "restart" the senescent cell cycle thereby activating cells which were otherwise damaged or dormant. The end result being a more "youthful" individual. This is evidenced by the growth or re-growth of colored (rather than gray) body hair, increased muscle mass, improved erectile function, improved salivary production, etc.

In one embodiment of the present invention there is a composition comprising: 1-methylfolate; methylcobalamin; n-acetylcysteine; pterostilbene; and nicotinamide riboside.

In yet another embodiment of the present invention there is a composition comprising: about 1 mg to about 15 mg of 1-methylfolate; about 0.25 mg to about 10 mg of methylcobalamin; about 100 mg to about 1000 mg of n-acetylcysteine; about 10 mg to about 100 mg of pterostilbene; and about 50 mg to about 500 mg of nicotinamide riboside.

In yet another embodiment of the present invention there is a method of improving an individual's vitality and health, the method comprising the steps of: administering a composition comprising: about 1 mg to about 15 mg of 1-methylfolate, about 0.25 mg to about 10 mg of methylcobalamin, about 100 mg to about 1000 mg of n-acetylcysteine, about 10 mg to about 100 mg of pterostilbene, and about 50 mg to about 500 mg of nicotinamide riboside.

In general, the present invention succeeds in conferring the following, and others not mentioned, benefits and objectives.

It is an object of the present invention to provide a composition that rejuvenates the body of a user.

It is an object of the present invention to provide a composition that improves at least hair color, muscle mass, salivary production, and vascular function.

It is an object of the present invention to provide a composition that stimulates the cell life cycle.

It is an object of the present invention to provide a composition that contains at least 1-methylfolate, methylcobalamin, n-acetylcysteine, pterostilbene, and nicotinamide riboside.

It is an object of the present invention to provide a composition that may be taken orally.

It is an object of the present invention to provide a composition that has minimal, if any, adverse side effects.

It is an object of the present invention to provide a composition that stimulates cell protein generation.

It is an object of the present invention to provide a composition that is safe and effective.

DETAILED DESCRIPTION OF THE EMBODIMENTS

Reference will now be made in detail to each embodiment of the present invention. Such embodiments are provided by way of explanation of the present invention, which is not intended to be limited thereto. In fact, those of ordinary skill in the art may appreciate upon reading the present specification that various modifications and variations can be made thereto.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

The term "about" is intended to mean the described amounts with a variance of ±10% of the range of the amount (by weight) of the composition. For example, a described "about 1 mg to about 15 mg" means that the amounts may be from 0.9 mg to 1.1 mg on the lower bound and about 13.5 mg to 16.5 mg on the upper bound of the described range. Single amounts (by weight) provided, preceded by the term "amount," also fall under the ±10% variance.

The composition, as described herein, may be taken orally or via other acceptable channels such as but not limited to transcutaneous, transmucosal, intravenous, or the like or some combination thereof. The form factor of the composition may also vary and may include but not be limited to a beverage, a capsule, a tablet, or a powder, or the like or some combination thereof.

Generally, the composition comprises 1-methylfolate, methylcobalamin, n-acetylcysteine, pterostilbene, and nicotinamide riboside. This composition may be taken once daily (per 24 hour period) and may be taken in the morning or evening hours. In some embodiments the 1-methylfolate, methylcobalamin, and n-acetylcysteine are taken in conjunction with one another once day, whereas the pterostilbene and nicotinamide riboside are taken twice daily with one of the two doses being taken in conjunction with the 1-methylfolate, methylcobalamin, and n-acetylcysteine.

In another embodiment, the composition of 1-methylfolate, methylcobalamin, n-acetylcysteine, pterostilbene, and nicotinamide riboside may be taken with metoprolol tartrate, omeprazole, acetylsalicylic acid, simvastatin, and clopidogrel. Each of the elements of the composition may be taken individually or may be taken in combination with one another (e.g. tablet, capsule, etc.). Various combinations of the components, which are too numerous to describe herein, are contained under the purview of this invention.

In one embodiment of the present invention the composition comprises about 1 mg to about 15 mg of 1-methylfolate; about 0.25 mg to about 10 mg of methylcobalamin; about 100 mg to about 1000 mg of n-acetylcysteine; about 10 mg to about 100 mg of pterostilbene; and about 50 mg to about 500 mg of nicotinamide riboside. The composition may further comprise about 10 mg to about 50 mg of metoprolol tartrate, about 20 mg to about 80 mg of omeprazole, about 40 mg to about 100 mg of acetylsalicylic acid, about 20 mg to about 60 mg of simvastatin, and about 40 mg to about 100 mg of clopidogrel.

More preferably the composition comprises about 6 mg of 1-methylfolate, about 2 mg of methylcobalamin, about 600 mg of n-acetylcysteine, about 250 mg of nicotinamide riboside, about 50 mg of pterostilbene. The composition may further provide for about 25 mg of metoprolol tartrate, about 40 mg of omeprazole, about 81 mg of acetylsalicylic acid, about 40 mg of simvastatin, and about 75 mg of clopidogrel. In some embodiments the composition provides for about 500 mg of nicotinamide riboside, about 100 mg of pterostilbene since these components may be taken twice daily as noted above. In yet other embodiments the composition provides for about 50 mg of metoprolol tartrate, about 80 mg of omeprazole, about 162 mg of acetylsalicylic acid, about 80 mg of simvastatin, and about 150 mg of clopidogrel since these components may be taken twice daily as noted above.

In yet another embodiment of the present invention there is a method of improving an individual's vitality and health, the method comprising the steps of: administering a composition comprising: about 1 mg to about 15 mg of 1-methylfolate, about 0.25 mg to about 10 mg of methylcobalamin, about 100 mg to about 1000 mg of n-acetylcysteine, about 10 mg to about 100 mg of pterostilbene, and about 50 mg to about 500 mg of nicotinamide riboside. The composition may be further provided as described herein.

Generally, each of the components is administered daily but each, either singularly or in combination with one another, may be taken up to three times per day. This regimen is preferably continued as needed and may be required to be administered for 8-12 weeks before noticeable results are seen by the user.

The compositions and methodologies herein may result in the growth and coloration (as opposed to gray) of body hair, stiffening of fingernails, increased salivary production, increased eye lubrication, increased erectile performance, increased muscle mass, and smoother skin.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A composition consisting of:
   1-methylfolate;
   methylcobalamin;
   n-acetylcysteine;
   pterostilbene;
   nicotinamide riboside;
   metoprolol tartrate;
   omeprazole;
   acetylsalicylic acid;
   simvastatin; and
   clopidogrel.

2. The composition of claim 1 wherein the composition has about 6 mg of 1-methylfolate.

3. The composition of claim 1 wherein the composition has about 2 mg of methylcobalamin.

4. The composition of claim 1 wherein the composition has about 600 mg of n-acetylcysteine.

5. The composition of claim 1 wherein the composition has about 250 mg of nicotinamide riboside.

6. The composition of claim 1 wherein the composition has about 50 mg of pterostilbene.

7. The composition of claim 1 wherein the composition has about 25 mg of metoprolol tartrate, about 40 mg of omeprazole, about 81 mg of acetylsalicylic acid, about 40 mg of simvastatin, and about 75 mg of clopidogrel.

8. A composition consisting of:
   about 1 mg to about 15 mg of 1-methylfolate;
   about 0.25 mg to about 10 mg of methylcobalamin;
   about 100 mg to about 1000 mg of n-acetylcysteine;
   about 10 mg to about 100 mg of pterostilbene; and
   about 50 mg to about 500 mg of nicotinamide riboside.

9. The composition of claim 8 wherein the composition has about 5 mg to about 10 mg of 1-methylfolate, about 1 mg to about 5 mg of methylcobalamin, about 400 mg to about 750 mg n-acetylcysteine, about 40 mg to about 60 mg of pterostilbene, and about 150 mg to about 300 mg of nicotinamide riboside.

10. A method of improving an individual's vitality and health, the method comprising the steps of:
    administering, to the individual, a composition consisting of:
    about 1 mg to about 15 mg of 1-methylfolate,
    about 0.25 mg to about 10 mg of methylcobalamin,
    about 100 mg to about 1000 mg of n-acetylcysteine,
    about 10 mg to about 100 mg of pterostilbene, and
    about 50 mg to about 500 mg of nicotinamide riboside.

11. The method of claim 10 wherein the composition is administered orally.

12. The method of claim 10 wherein the composition is administered once in a twenty four hour period.

13. The method of claim 10 wherein the composition is in the form of a beverage, capsule, tablet, or powder.

14. The method of claim 10 wherein the composition has about 6 mg of 1-methylfolate, about 2 mg of methylcobalamin, about 600 mg of n-acetylcysteine, about 50 mg of pterostilbene, and about 250 mg of nicotinamide riboside.

* * * * *